US008315692B2

(12) United States Patent
Sheinis

(10) Patent No.: US 8,315,692 B2
(45) Date of Patent: Nov. 20, 2012

(54) MULTI-SPECTRAL IMAGING SPECTROMETER FOR EARLY DETECTION OF SKIN CANCER

(76) Inventor: Andrew I. Sheinis, Madison, WI (US)

( * ) Notice: Subject to any disclaimer, the term of this patent is extended or adjusted under 35 U.S.C. 154(b) by 895 days.

(21) Appl. No.: 12/066,982

(22) PCT Filed: Feb. 22, 2008

(86) PCT No.: PCT/US2008/054743
§ 371 (c)(1),
(2), (4) Date: Mar. 14, 2008

(87) PCT Pub. No.: WO2008/103918
PCT Pub. Date: Aug. 28, 2008

(65) Prior Publication Data
US 2010/0063402 A1    Mar. 11, 2010

Related U.S. Application Data

(60) Provisional application No. 60/891,146, filed on Feb. 22, 2007.

(51) Int. Cl.
*A61B 6/00* (2006.01)
(52) U.S. Cl. .......................... 600/476; 600/473
(58) Field of Classification Search .................. 600/476, 600/477
See application file for complete search history.

(56) References Cited

U.S. PATENT DOCUMENTS

| 5,297,555 | A |   | 3/1994 | Martens et al. |
| 5,782,770 | A |   | 7/1998 | Mooradian et al. |
| 5,953,477 | A | * | 9/1999 | Wach et al. .................... 385/115 |
| 6,069,689 | A | * | 5/2000 | Zeng et al. ....................... 356/73 |
| 2006/0072109 | A1 |   | 4/2006 | Bodkin et al. |

FOREIGN PATENT DOCUMENTS

| DE | 29711327 U1 | 11/1997 |
| WO | WO 2006/107947 A | 10/2006 |

OTHER PUBLICATIONS

International Search Report, PCT Application No. PCT/US2008/054743, dated Jul. 21, 2008, ISA/EPO, 2280 HV Rijswijk, NL.
Carrasco, et al., Hyperspectral imaging applied to medical diagnoses and food safety, SPIE Proceedings, 2003, pp. 215-221, Bellingham, Washington.
Bogdanov, V. et al., Parallel confocal and complete spectrum imager for fluorescent detection of high-density microarray, Proceedings of the SPIE, Jan. 24, 1999, vol. 3605, pp. 298-307, Bellingham, Washington.
Martin, E. Martin, et al., Development of an Advanced Hyperspctral Imaging (HIS) System with Applications for Cancer Detection, Annals of Biomedical Engineering, Jun. 2006, vol. 34, No. 6, pp. 1061-1068, Biomedical Engineering Society, Landover, MD.

* cited by examiner

*Primary Examiner* — Jacqueline Cheng

(57) ABSTRACT

An imaging spectrometer provides substantially simultaneous areal spectroscopy and image generation to provide improved analysis of possible skin cancer.

19 Claims, 3 Drawing Sheets

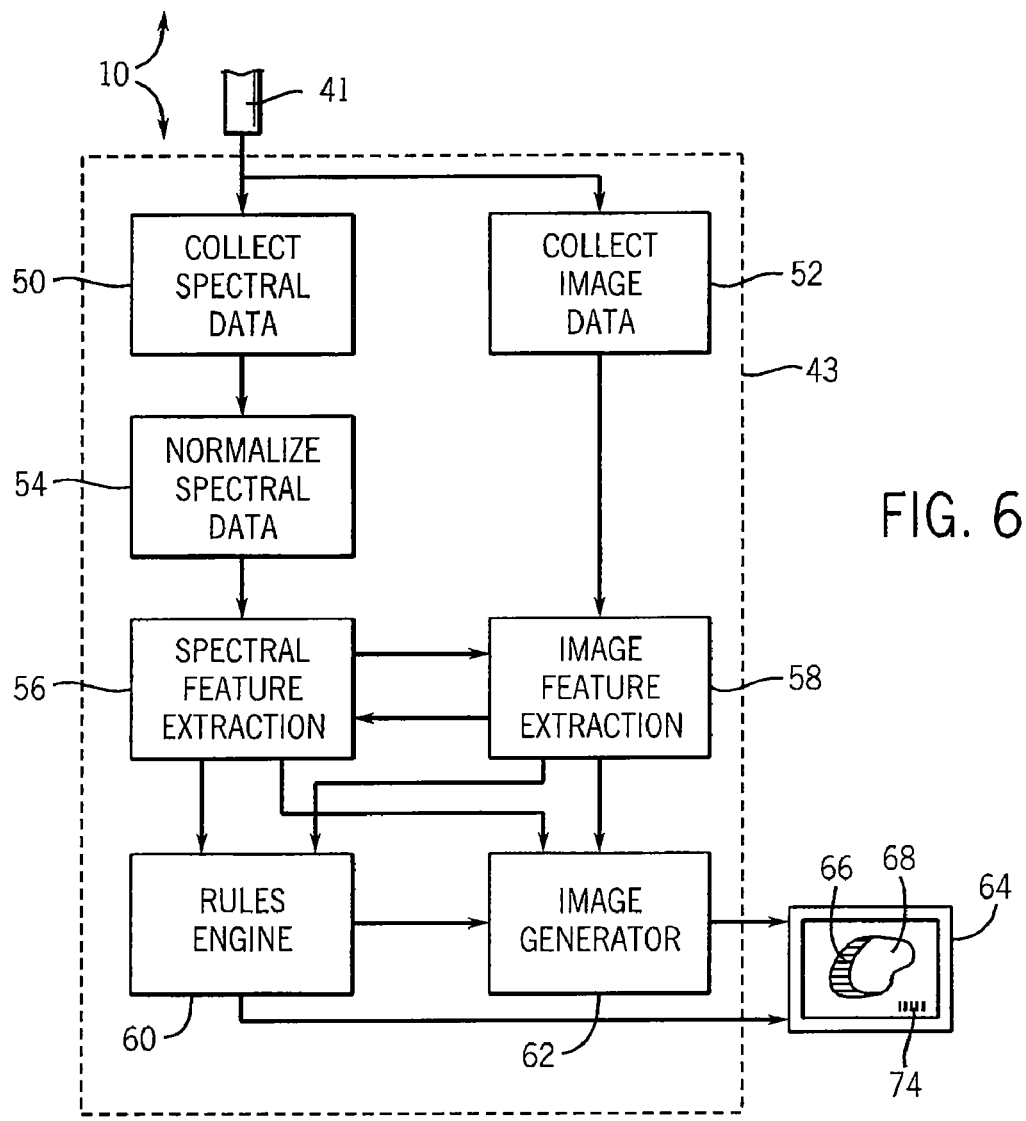
FIG. 6
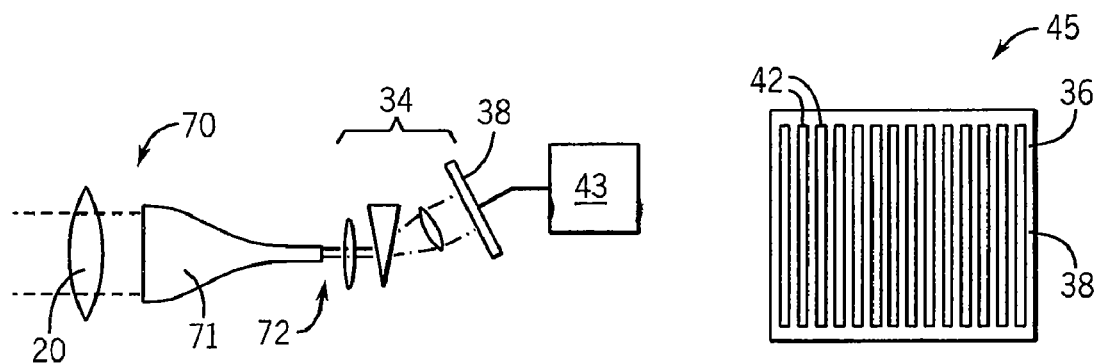
FIG. 7
FIG. 8

MULTI-SPECTRAL IMAGING SPECTROMETER FOR EARLY DETECTION OF SKIN CANCER

CROSS REFERENCE TO RELATED APPLICATION

This application claims the benefit of U.S. Provisional Application 60/891,146, filed Feb. 22, 2007, the disclosure of which is incorporated herein by reference.

BACKGROUND OF THE INVENTION

The present invention relates to medical imaging equipment and in particular to an imaging spectrometer for detection of skin cancer.

The early detection of skin cancer largely relies on visual inspection of the skin and, in particular, on identification of skin patches with asymmetrical outlines, border irregularity, mottled colors, and diameters larger than a 6 mm (the skin cancer "ABC's"). While visual inspection is particularly well suited to cancer of the skin, the human eye's ability to distinguish among light frequencies is limited. The human eye is sensitive to three broad frequency bands whose relative intensities create the perception of many colors. Frequencies outside those bands are not perceptible, different frequencies within those bands may not be distinguishable, and single frequencies in areas of overlap of the bands can not be reliably distinguished from the effect of two different frequencies of light within each band.

The visually observable characteristics of skin cancer cells provide reason to believe that spectral information could provide improved cancer detection. U.S. Pat. No. 4,515,165, issued May 7, 1985, describes a medical imaging system in which cancerous tissue is illuminated with different frequencies of light to provide for multi-spectral imaging of tissue. U.S. Pat. No. 5,782,770 issued Jul. 21, 1998 describes an alternative approach in which polychromatic light illuminates the tissue and a scanning slit spectrograph is used to analyze the reflected light. The spectrograph provides "hyperspectral" imaging providing spectral readings at multiple frequencies with a spectral resolution of less than 10 nm of wavelength.

In both of these systems the imaging process is delayed by either the need to switch between colors or to scan a slit over an area of the imaged object. This delay creates the potential for misregistration of the image and spectrum and possible distortion of the image or spectrum if there is any movement during the acquisition process. To the extent that the switching of colors or slit scanning process require moving mechanical components, the ability to manufacture a rugged, portable and practical field device, may be adversely affected.

SUMMARY OF THE INVENTION

The present invention provides an imaging system that may acquire high resolution spectral and image data in one step, avoiding image registration or image distortion problems, or the need for moving components. The invention employs an optical system that remaps light from normally contiguous elements of an object onto a planar detector in a way that provides interstitial space on the detector between the light from each object element. A dispersion element then generates a spectrum extending into the interstitial space so that the detector simultaneously captures imaging and spectral information. Eliminating the need for moving parts allows perfectly registered and skew-less image and spectral analysis of the skin and allows the practical construction of a rugged handheld device.

Specifically then, the present invention provides an instrument for detection of skin cancer having a multi-spectral illumination source for illuminating a region of skin and a solid-state image sensor providing multi-spectral sensitivity for imaging that region. An optical system receives light from the illuminated region of skin to optically remap regions of an object of the region onto an image sensor as discontiguous regions, and a dispersion element positioned between the image sensor and the optical system projects spectra of the discontiguous regions onto the image sensor outside of the discontiguous regions. An image processor receives the spectra and analyzes the spectra to identify cancerous features.

Thus, it is one aspect of at least one embodiment of the invention to provide a spectrometer suitable for clinical use where mechanical scanning elements, which may be cumbersome and unreliable, are eliminated in favor of a fixed optical system.

The light may be remapped from contiguous regions of the skin and that light of the discontiguous regions may fully characterizes the light from the contiguous region.

It is thus an aspect of at least one embodiment of the invention to provide a system that samples all tissue within the region so that possibly small areas of cancer are not missed.

The identification of cancerous features may provide a matching of spectral characteristics of the spectra to spectral characteristics of known skin cancer types.

It is thus an aspect of at least one embodiment of the invention to allow spectral identification of possible skin cancer.

The identification of cancerous features may provide an image that accentuates regions having cancerous features.

It is thus an aspect of some embodiments of the invention to provide an image that may be easily reviewed and evaluated by a physician providing spectral data as an overlay.

The dispersion element may be a prism.

It is therefore a feature of at least one embodiment of the invention to provide a system that produces an unambiguous mapping of spectra on the image detector surface without the repeating spectrum orders that may be produced by an optical grating.

The optical system may be a micro lens array.

It is thus one feature of one embodiment of the invention to provide a simple optical system for providing the needed remapping.

The optical system may be a set of light guides.

It is a feature of at least one embodiment of the invention to provide a flexible optical system that may provide an arbitrary remapping of light for optimal spectral detection.

The multi-spectral illumination source may use light emitting diodes and the system may normalize the acquired spectra against a spectrum of the light emitting diodes before analyzing the spectra to identify cancerous features.

It is thus a feature of at least one embodiment of the invention to provide a system that may work with cool and long-lived light emitting diodes that nevertheless have a variable light spectrum.

The image processor may receive the spectra to reconstruct the spectra into an image, and the image processor may process at least one of the spectra and the image according to information derived from the other one of the spectra and image.

It is thus an aspect of at least one embodiment of the invention to allow analysis of the spectra and the image to each be informed by the analysis of the other.

The image may be processed to identify likely cancerous tissue and likely non-cancerous tissue to allow comparison of spectra in the cancerous tissue and non-cancerous tissue for the identification of cancerous tissue.

It is thus a feature of at least one embodiment of the invention to allow the image to be used to identify baseline non-cancerous tissue for the improved spectral detection of cancerous tissue.

The spectra may be used to identify a boundary of spectrally different tissue in the image for evaluation of spatial features of the boundary in the image.

It is thus another feature of at least one embodiment of the invention to allow improved spatial identification of the outline of a patch of differentiated tissue on skin through the use of spectral analysis.

The instrument may be hand held and may further include a focus guide holding the instrument unit at a fixed distance from the skin when one edge of the focus guide is placed against the skin.

It is thus another feature of the invention to provide a system that may rapidly acquire image and spectral data in a handheld implementation for convenient use by a physician or at home.

The optical system may simultaneously measure an areal image of the region of the skin composed of multiple contiguous elements and the spectra of the multiple contiguous elements.

Thus it is an aspect of at least one embodiment of the invention to provide for a system that provides for perfect registration between an image and its spectral measurement for improved analysis of both.

These particular features and advantages may apply to only some embodiments falling within the claims and thus do not define the scope of the invention.

BRIEF DESCRIPTION OF THE DRAWINGS

FIG. 6 is a block diagram of a processor associated with the unit of FIG. 1 receiving image and spectrum data to provide analysis of a skin tissue;

FIG. 7 is a figure similar to that of FIG. 5 showing an alternate optical remapper employing light guides; and FIG. 8 is a spectrum plane similar to the spectrum plane of FIG. 4 but as created by the optical system of FIG. 7.

DETAILED DESCRIPTION OF THE PREFERRED EMBODIMENT

Figure 1:
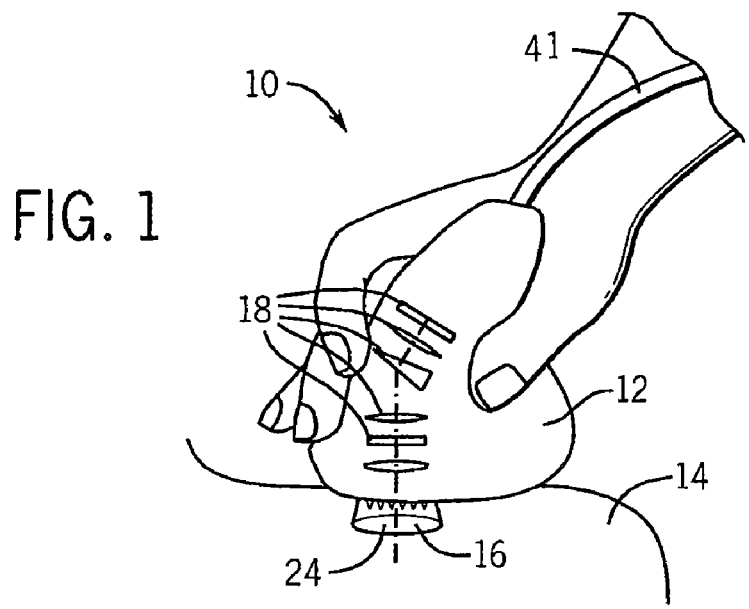
FIG. 1 is a perspective view of an instrument, according to one embodiment of the present invention, showing a focus guide pressed against the skin and, in phantom, the path of light received from the patient's skin through portions of the optical system.

Referring now to FIG. 1, an imaging spectrometer 10 of the present invention may provide for a housing 12 that may be manipulated by hand to view an object area 24 of the skin of a patient 14.

A tubular focus guide 16 may extend from the bottom of the housing 12 so that an optical assembly 18 within the housing may be precisely located with respect to the object area 24 at a desired focal distance.

Figure 2:
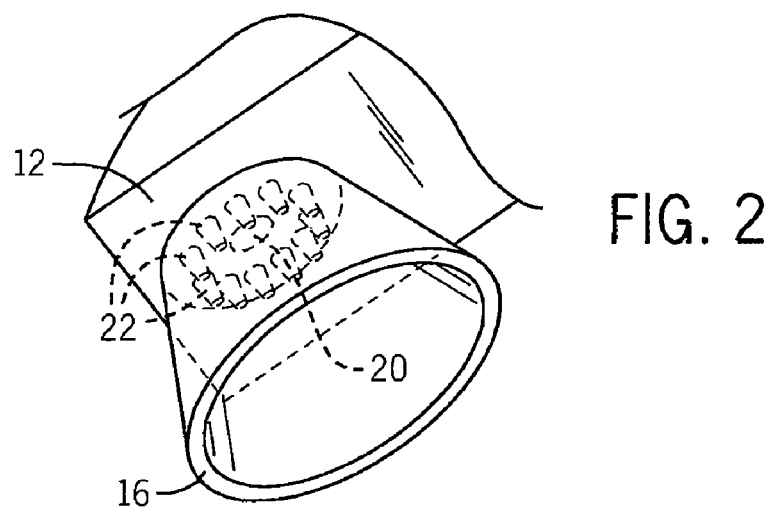
FIG. 2 is a bottom plan view of the instrument of FIG. 1 showing an illuminating ring of light emitting diodes within the focus guide and surrounding an objective lens.

Referring also to FIG. 2, the tubular focus guide 16 may surround an objective lens 20 of the optical assembly 18, which is preferably a fixed focus lens, whose imaging characteristics match the length of the tubular focus guide 16. A series of different fixed focal length lenses or a variable focus lens and auto focusing mechanism may also be used in an alternative embodiment.

A set of light emitting diodes 22 may be arranged in a ring about the objective lens 20 inside the tubular focus guide 16 to provide even illumination of the object area 24 on skin of the patient within the tubular focus guide 16. Alternatively standard incandescent type or fluorescent bulbs may be used. The focus guide 16 may be transparent for ease of positioning on the imaging spectrometer 10 over a desired object area 24 or may be opaque to block interference from external illumination sources with location of the focus guide over the desired object area 24 being done by viewing of an electronic image to be described.

The imaging spectrometer 10 may be wholly contained within the housing 12 or may transmit image data via a cord 41 or a wireless transmitter (not shown) to remote image processing circuitry 43, as will be described. All or part of the analysis to be described may be done remotely, for example, by transmitting data directly to the physician's office for processing or review.

Figure 3:
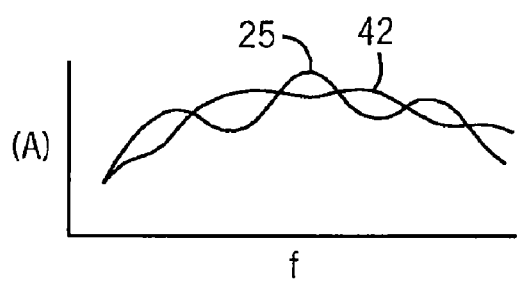
FIG. 3 is a spectrum measured by the instrument of FIG. 1 superimposed on the spectrum of the light from the light emitting diodes such as may be used to normalize the former.

Referring now to FIG. 3, the light emitting diodes 22 or other illumination source may produce light having a non-uniform spectrum 25 being a function of the construction of white light emitting diodes (made up of three colored light emitting diodes) as well as variations in the manufacturing process. This spectrum 25 may be measured and used for a normalization as will be described below.

Figure 4:
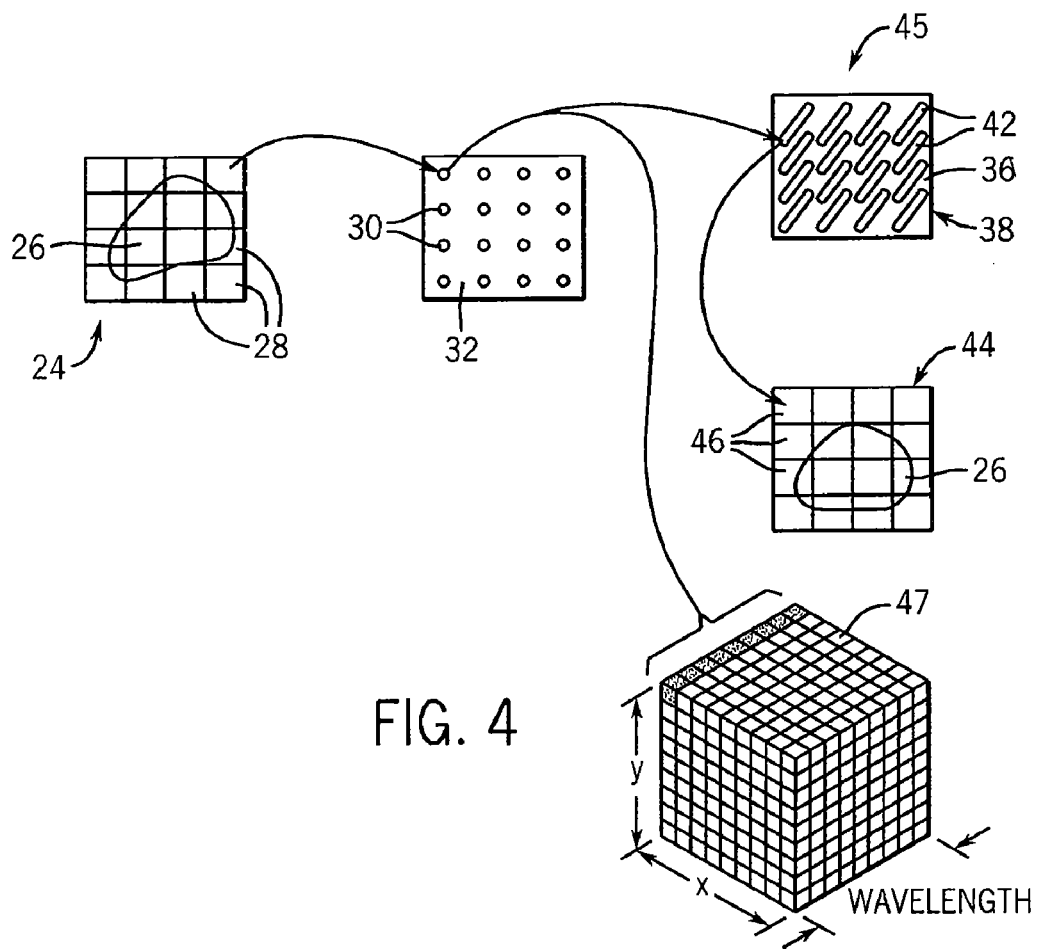
FIG. 4 is a flow chart showing the various optical planes generated in the present invention including an object plane on the skin, a pupil plane used for the spectral analysis and which may be mapped to a spectrum plane, and a second image plane on an image detector.
Figure 5:
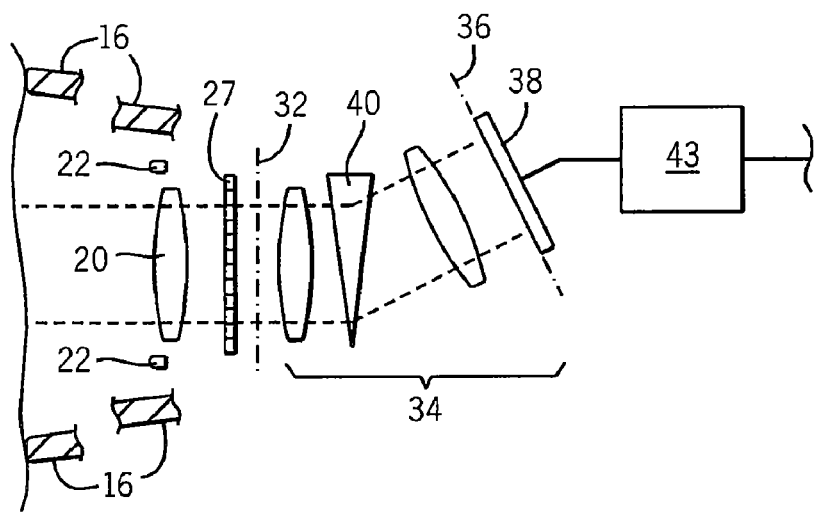
FIG. 5 is a schematic representation of the optical elements of the instrument of FIG. 1 showing a micro lens array used as an optical remapper and a prism used as the dispersion element.

Referring now to FIGS. 4 and 5, the objective lens 20 may be aligned and focused on the object area 24 of the skin in the area of a suspicious feature 26. The object area 24 is then illuminated by the light emitting diodes 22 and the reflected light is collected by the objective lens 20 and passed to a micro-lens array 27. The micro-lens array is a set of lenses, either standard or anamorphic lenses, arranged contiguously over an area to capture substantially all the light passing through the area and provide multiple focal points, one focal point associated with each lens.

The micro-lens array 27 thereby effectively divides the object area 24 formed of contiguous object elements 28 and remaps the light from the continuous object elements 28 to corresponding light points 30 in a pupil plane 32. Each light point 30 generally has a smaller spatial extent than the object elements 28 provided the object elements 28 are sufficiently small to present an essentially constant field with no or little spatial variation. This constant field of each object element 28 is transformed by each lens of the micro-lens array 27 to a single, intensity value at the light point 30. Thus, light points 30 provide spatially compressed versions of object elements 28 retaining the same spectral content and total energy of the object elements 28. In this embodiment, substantially all of the light from the object area 24 is captured and remapped to the pupil plane 32.

The pupil plane 32 is aligned with a first object plane of a spectrometer 34 which receives the light points 30 and disperses them according to frequency onto an image (spectrum) plane 36 aligned with the face of an image detector 38, for example, a charge coupled device (CCD) detector, which may be a broadband monochromatic sensor. The dispersion in this case may be done by means of a prism 40 eliminating the multiple orders of spectrum produced by a grating; however, the invention contemplates that a grating may also be used by proper design of the spectrometer 34.

The dispersion axis of the prism 40 is oriented at an angle with respect to rows and columns of lenses of the micro-lens array 27 so that the light from each of the light points 30 in the pupil plane 32 are spread into a separate spectra 42 extending in interleaved fashion without interference with each other on the surface of the image detector 38.

Spectral data 45, representing intensity values acquired from the image detector 38 at defined locations corresponding to particular frequencies of light in the spectra 42, are received by image processing circuitry 43. The pixel size of the image detector 38 is sufficiently small to allow multipoint measurements (e.g., 16-100 measurements) of each spectrum 42 permitting multiple different frequency bands for each object element 28 of the object area 24 to be resolved and detected. This spectral data 45 provides intensity and location information that may be used to fully characterize the spectra 42.

The spectra 42 each provide one row of a data cube 47 where position along the row provides intensity values as a function of wavelength or frequency. The location of the row in the data cube 47, in perpendicular coordinates x and y, correspond to the x and y location of the object elements 28 in the object area 24 forming the light points 30. Thus, one data acquisition may produce a data cube 47 of spectral and spatial data.

Additional discussion of the operation of a spectrometer suitable for use in the present invention for spectrometer 34, is described in detail in U.S. patent application 2006/0072109, naming the inventor of this application, filed Apr. 6, 2006 and hereby incorporated by reference.

Referring still to FIGS. 4 and 5, spectral data 45 of the spectrum plane 36 is provided to image processing circuitry 43, as will be described in additional detail below. The image processing circuitry 43 may be incorporated into the housing 12 of the imaging spectrometer 10 or in a remote computer connected to the imaging spectrometer 10 by means of a cable 47 or wireless systems such as Bluetooth transmitters and the like.

Referring to FIGS. 4 and 6, the imaging spectrometer 10 processes the spectral data 45 to generate an electronic image 44 by integrating the energy in each spectra 42 over frequency and mapping that total energy, according to the known geometry of the optical assembly 18, back to corresponding image elements 46 having the same geometrical relationship as the object element 28. No image data is lost in this process (in terms of feature resolution) provided that the object elements 28 are less than half the size of any feature desired to be resolved. Appropriate selection of the micro-lens array 27 may ensure this condition.

The electronic image 44 generated by the image processing circuitry 43 may be a monochromatic image or may be a color image, the later generated by partitioning each spectrum 42 into bands approximating the three primary additive colors. Alternatively, the electronic image may be constructed from other portions of the spectra 42 to create false color images or band limited images. Similarly, weighting may be applied to the colors of the spectra to provide color-weighted images.

It will be understood from the above description that the imaging spectrometer 10 may thus receive light in each frame of data, from the entire object area 24 to produce at once both spectral data 45 and an electronic image 44 for all the contiguous object elements 28 in the object area 24 ensuring accurate registration between the electronic image 44 and the spectral data 45 with reduced distortion caused by motion of the imaging spectrometer 10.

Referring now to FIG. 6, the image processing circuitry 43 may further process the collected multipoint spectral data 45, as indicated by process block 50, and multipoint electronic image 44, as indicated by process block 52. This processing may be by means of an electronic computer (not shown) executing a stored program to process digital values representing the spectral data 45 and the electronic image 44.

First, as indicated by process block 54, and referring again to FIG. 3, each spectrum 42 of the spectral data 45 (shown in FIG. 4) may be normalized to the spectrum 25 of the known incident light of the light emitting diodes 22 or other light source. This normalization may simply divide each point of the spectral data 45 for each spectrum 42 by the corresponding point of the spectrum 25 to compensate for changes in intensity of the illumination at different frequencies.

At process block 56, the corrected spectral data 45 may be analyzed to extract spectral features. In the simplest case, predefined and stored reference spectrum frequency bands and normalized intensities for those bands, for known healthy and cancerous tissues, may be compared to corresponding bands and intensities of the tissue imaged by the present invention. Both the reference and actually measured spectral values may be normalized to have comparable total light energy, the total light energy being the integral of the spectra between two predetermined frequencies. This approach allows different spectral bands to be isolated or given greater weight in the analysis process. Alternatively, a library of normalized reference spectra for known healthy and cancerous tissues may be correlated with the measured spectra to identify a closest match.

The spectral feature extraction process may be augmented by the step of taking an initial scan of the patient's skin near the region of the suspicious feature 26 but believed to be cancer free, or using regions in the data image away from the suspicious feature that are believed to be cancer free to provide a patient reference spectrum that may be used to compensate (for example, by looking at only spectral differences between these two spectra) for variations in underlying tissue pigmentation among individuals and lighting differences between frames. In this latter case, the reference spectral values may also be difference values.

As an alternative to identifying separate cancer free areas, the image processor 43 may normalize all spectra to an average of an entire frame, and in this way correct for variations due to illumination and skin color, discolorations in the skin and externally scattered light under the assumption that the image area is large enough to contain a healthy skin sample.

The present invention contemplates that the spectral feature extraction may be informed by the electronic image 44 and, in particular, by an image feature extraction performed at process block 58 in which the area of the suspicious feature 26 is demarcated using standard image processing techniques such as morphological analysis. In this case, the electronic image 44 may be used to identify regions of likely healthy tissue and regions of suspicious tissue so that the spectral features of these two regions may be compared as described above automatically, or with operator oversight. In this case, the image guides the spectral analysis. The image may also be used to provide areas over which the spectra will be averaged to increase statistical reliability or to provide weighting of the significance of spectral data 45 from different regions.

Alternatively, the image feature extraction of process block 52 may be used independently to assess a demarcated area of the skin for cancer using the image based tests of asymmetry, irregular border, color and diameter (the ABC's of skin cancer detection). This demarcation process, in turn, may be informed by the spectral analysis of process block 56, for example, by defining the boundary of the suspicious feature 26 by spectral features that may not be readily apparent to the human eye.

Information from the image feature extractor of process block 58 and the spectral feature extraction of process block 56 may be weighted and combined by a rules engine 60 operating using a set of expert rules, templates or statistically derived algorithms to identify whether cancer is likely based on both spectral and image measurements.

In addition, the information from the spectral feature extraction of process block 56 and the image feature extractor of process block 58 may be provided to an image generator 62 which may display on a display 64 an image 66 showing a conventional image of the object area 24 as would be visible to a human observer, and a false color image 68 superimposed on that image either identifying particular spectral features or identifying regions, per the rules engine 60, where cancerous tissue may be likely. One or more quantitative values 74 may also be displayed indicating for example skin area, confidence values and the like.

Referring now to FIG. 7, in an alternative embodiment of the present invention, the objective lens 20 may be followed by a fiber optic remapper 71. The fiber optic remapper 71 may have a front face 70 consisting of the bundled ends of optical fibers arranged over a rectangular area at the image plane of the objective lens 20 to receive light from the objective lens for predetermined object elements 28. The optical fibers are then routed separately to a rear face 72 where the ends of the fibers have been rearranged into a single continuous line. The rear face 72 of the fiber optic remapper 71 sits at the image plane of the spectrometer 34 such as that described above. In this case, and referring FIG. 8, the spectra 42 may extend an arbitrary distance, providing potentially greater spectral resolution. Other methods of "slicing" the image, including the use of mirror arrays and the like, are also envisioned.

In yet a further embodiment, (not shown) the remapping may simply sample small areas of the object plane by blocking other areas. This is not a preferred embodiment, but can provide many of other benefits of the invention.

While the preferred embodiment reconstructs image data from the spectral data, the invention also contemplates that the image could be generated using a beam splitter and second image detector 38.

It is specifically intended that the present invention not be limited to the embodiments and illustrations contained herein, but include modified forms of those embodiments including portions of the embodiments and combinations of elements of different embodiments as come within the scope of the following claims.

I claim:

1. An instrument for detection of skin cancer comprising:
a multi-spectral illumination source configured to simultaneously illuminate a two-dimensionally dispersed area over a region of skin;
a solid-state image sensor configured to provide multi-spectral sensitivity over a contiguous area;
a dispersion element;
an optical system positioned with respect to the solid-state image sensor to receive light from the illuminated region of skin over the two-dimensionally dispersed area and configured to optically remap the light from the two-dimensionally dispersed area onto a plane as discontiguous regions dispersed in two dimensions over the plane, absent the dispersion element, wherein the image sensor is positioned at and aligned with the plane and the discontiguous regions are produced simultaneously;
wherein the dispersion element is positioned between the image sensor and the optical system and configured to project spectra of the light from the skin, the spectra extending outside of the discontiguous regions;
a non-transitory computer readable medium configured with instructions to analyze the spectra to identify cancerous features; and
an image processor circuit configured to receive the spectra and operating to execute the instructions to analyze the spectra at multiple points over the illuminated region of skin to identify cancerous features.

2. The instrument of claim 1 wherein the multi-spectral illumination source and the optical system are configured to cooperate so that light from a contiguous region of the skin is fully characterized by light of the discontiguous regions.

3. The instrument of claim 1 wherein the non-transitory computer readable medium is further configured with instructions to identify cancerous features by providing a matching of spectral characteristics of the spectra to spectral characteristics of known skin cancer types.

4. The instrument of claim 1 wherein the non-transitory computer readable medium is further configured with instructions to provide an image accentuating regions having cancerous features.

5. The instrument of claim 1 wherein the dispersion element is a prism.

6. The instrument of claim 1 wherein the optical system is a micro lens array.

7. The instrument of claim 1 wherein the optical system is a set of light guides.

8. The instrument of claim 1 wherein the multi-spectral illumination source is light emitting diodes and wherein the non-transitory stored program of instructions further executes to normalized the spectra to a spectrum of the light emitting diodes prior to analyzing the spectra to identify cancerous features.

9. The instrument of claim 1 wherein the non-transitory computer readable medium is further configured with instructions to receive the spectra to reconstruct at least a portion of the spectra into an image and wherein the image processor processes at least one of the spectra and the image according to information derived from an other of the spectra and image to analyze the spectra at multiple points over the illuminated region of skin based on the frequency components of the spectra and the location of the spectra to identify cancerous features.

10. The instrument of claim 1 wherein the non-transitory computer readable medium is further configured with instructions to produce an image of the skin and to identify likely cancerous tissue and likely non-cancerous tissue from the image to identify spectra to be compared in at least one of the cancerous tissue and non-cancerous tissue for the identification of cancerous tissue.

11. The instrument of claim 10 wherein the non-transitory computer readable medium is further configured with instructions process the spectra to identify a boundary of spectrally different tissue in the image for evaluation of spatial features of the boundary in the image.

12. The instrument of claim 1 wherein the instrument is configured so that it may be hand held and further including a focus guide holding the instrument unit at a fixed distance from the skin when one edge of the focus guide is placed against the skin.

13. An instrument for detection of skin cancer comprising:
- a multi-spectral illumination source adapted to simultaneously illuminate a two-dimensionally dispersed area over a region of skin with multi-spectral light;
- a solid-state image sensor providing multi-spectral light sensitivity;
- an optical system configured to project the light from a region of skin on the solid-state image sensor to allow the solid-state image sensor to simultaneously measure an areal image of the region of the skin composed of multiple contiguous elements and the spectra of the multiple contiguous elements;
- a non transitory computer readable medium configured with instructions to analyze the spectra to identify cancerous features; and
- an image processor circuit receiving the spectra and the image and operating to execute the instructions to identify cancerous features based on an analysis of spectra at multiple points over the illuminated region of skin.

14. The instrument of claim 13 wherein the optical system is a micro lens array.

15. The instrument of claim 13 wherein the optical system is a set of light guides.

16. The instrument of claim 13 wherein the multi-spectral illumination source is at least one light emitting diode and wherein the non-transitory computer readable medium is further configured with instructions to normalize the spectra to a spectrum of the light emitting diodes prior to analyzing the spectra to identify cancerous features.

17. The instrument of claim 13 wherein the non-transitory computer readable medium is further configured with instructions to produce an image of the skin and to identify likely cancerous tissue and likely non-cancerous tissue using the image, this identification used to identify spectra to be compared in at least one of the cancerous tissue and non-cancerous tissue for the identification of cancerous tissue.

18. The instrument of claim 13 wherein non-transitory computer readable medium is further configured with instructions to identify a boundary of spectrally different tissue using the spectra, and further using this evaluation for evaluation of spatial features of the boundary of the spectrally different tissue.

19. The instrument of claim 13 further including a focus guide holding the instrument at a fixed distance from the skin when one edge of the focus guide is placed against the skin.

* * * * *